(12) United States Patent
Kiani

(10) Patent No.: US 7,976,472 B2
(45) Date of Patent: Jul. 12, 2011

(54) NONINVASIVE HYPOVOLEMIA MONITOR

(75) Inventor: Massi E. Kiani, Laguna Niguel, CA (US)

(73) Assignee: Masimo Corporation, Irvine, CA (US)

( * ) Notice: Subject to any disclaimer, the term of this patent is extended or adjusted under 35 U.S.C. 154(b) by 1150 days.

(21) Appl. No.: 11/221,411

(22) Filed: Sep. 6, 2005

(65) Prior Publication Data
US 2006/0058691 A1 Mar. 16, 2006

Related U.S. Application Data

(60) Provisional application No. 60/607,562, filed on Sep. 7, 2004.

(51) Int. Cl.
*A61B 5/02* (2006.01)
(52) U.S. Cl. .......... 600/507; 600/504; 600/502
(58) Field of Classification Search .......... 600/500–502, 600/513, 323, 324, 371, 454
See application file for complete search history.

(56) References Cited

U.S. PATENT DOCUMENTS

| | | | |
|---|---|---|---|
| 4,859,056 A * | 8/1989 | Prosser et al. ................. | 356/41 |
| 4,960,128 A | 10/1990 | Gordon et al. | |
| 4,964,408 A | 10/1990 | Hink et al. | |
| 5,041,187 A | 8/1991 | Hink et al. | |
| 5,069,213 A | 12/1991 | Polczynski | |
| 5,119,814 A * | 6/1992 | Minnich ................... | 600/320 |
| 5,163,438 A | 11/1992 | Gordon et al. | |
| 5,337,744 A | 8/1994 | Branigan | |
| 5,431,170 A | 7/1995 | Mathews | |
| 5,452,717 A | 9/1995 | Branigan et al. | |
| 5,482,036 A | 1/1996 | Diab et al. | |
| 5,490,505 A | 2/1996 | Diab et al. | |
| 5,490,506 A * | 2/1996 | Takatani et al. ............... | 600/309 |
| 5,494,043 A | 2/1996 | O'Sullivan et al. | |
| 5,533,511 A | 7/1996 | Kaspari et al. | |
| 5,590,649 A | 1/1997 | Caro et al. | |
| 5,632,272 A | 5/1997 | Diab et al. | |
| 5,638,816 A | 6/1997 | Kiani-Azarbayjany et al. | |
| 5,638,818 A | 6/1997 | Diab et al. | |
| 5,645,440 A | 7/1997 | Tobler et al. | |
| 5,685,299 A | 11/1997 | Diab et al. | |
| D393,830 S | 4/1998 | Tobler et al. | |
| 5,743,262 A | 4/1998 | Lepper, Jr. et al. | |
| 5,758,644 A | 6/1998 | Diab et al. | |
| 5,760,910 A | 6/1998 | Lepper, Jr. et al. | |
| 5,769,785 A | 6/1998 | Diab et al. | |
| 5,782,757 A | 7/1998 | Diab et al. | |
| 5,785,659 A | 7/1998 | Caro et al. | |
| 5,791,347 A | 8/1998 | Flaherty et al. | |
| 5,810,734 A | 9/1998 | Caro et al. | |

(Continued)

OTHER PUBLICATIONS

Mohammad Goparvar, et al., "Evaluating the Relationship Between Arterial Blood Pressure Changes and Indices of Pulse Oximetric Plethysmography," Anesthesia-Analgesia 2002; 95:1686-1690.

(Continued)

*Primary Examiner* — Patricia C Mallari
*Assistant Examiner* — Michael D'Angelo
(74) *Attorney, Agent, or Firm* — Knobbe, Martens, Olson & Bear LLP

(57) ABSTRACT

A hypovolemia monitor comprises a plethysmograph input responsive to light intensity after absorption by fleshy tissue. A measurement of respiration-induced variation in the input is made. The measurement is normalized and converted into a hypovolemia parameter. An audible or visual indication of hypovolemia is provided, based upon the hypovolemia parameter.

17 Claims, 3 Drawing Sheets

U.S. PATENT DOCUMENTS

| | | | |
|---|---|---|---|
| 5,823,950 | A | 10/1998 | Diab et al. |
| 5,830,131 | A | 11/1998 | Caro et al. |
| 5,833,618 | A | 11/1998 | Caro et al. |
| 5,860,919 | A | 1/1999 | Kiani-Azarbayjany et al. |
| 5,890,929 | A | 4/1999 | Mills et al. |
| 5,904,654 | A | 5/1999 | Wohltmann et al. |
| 5,919,134 | A | 7/1999 | Diab |
| 5,934,277 | A * | 8/1999 | Mortz .......................... 600/323 |
| 5,934,925 | A | 8/1999 | Tobler et al. |
| 5,940,182 | A | 8/1999 | Lepper, Jr. et al. |
| 5,995,855 | A | 11/1999 | Kiani et al. |
| 5,997,343 | A | 12/1999 | Mills et al. |
| 6,002,952 | A | 12/1999 | Diab et al. |
| 6,011,986 | A | 1/2000 | Diab et al. |
| 6,027,452 | A | 2/2000 | Flaherty et al. |
| 6,036,642 | A | 3/2000 | Diab et al. |
| 6,045,509 | A | 4/2000 | Caro et al. |
| 6,067,462 | A | 5/2000 | Diab et al. |
| 6,081,735 | A | 6/2000 | Diab et al. |
| 6,088,607 | A | 7/2000 | Diab et al. |
| 6,110,522 | A | 8/2000 | Lepper, Jr. et al. |
| 6,129,675 | A * | 10/2000 | Jay .............................. 600/485 |
| 6,151,516 | A | 11/2000 | Kiani-Azarbayjany et al. |
| 6,152,754 | A | 11/2000 | Gerhardt et al. |
| 6,157,850 | A | 12/2000 | Diab et al. |
| 6,165,005 | A | 12/2000 | Mills et al. |
| 6,168,568 | B1 * | 1/2001 | Gavriely ....................... 600/529 |
| 6,184,521 | B1 | 2/2001 | Coffin, IV et al. |
| 6,206,830 | B1 | 3/2001 | Diab et al. |
| 6,229,856 | B1 | 5/2001 | Diab et al. |
| 6,236,872 | B1 | 5/2001 | Diab et al. |
| 6,256,523 | B1 | 7/2001 | Diab et al. |
| 6,263,222 | B1 | 7/2001 | Diab et al. |
| 6,278,522 | B1 | 8/2001 | Lepper, Jr. et al. |
| 6,280,213 | B1 | 8/2001 | Tobler et al. |
| 6,285,896 | B1 | 9/2001 | Tobler et al. |
| 6,334,065 | B1 | 12/2001 | Al-Ali et al. |
| 6,349,228 | B1 | 2/2002 | Kiani et al. |
| 6,360,114 | B1 | 3/2002 | Diab et al. |
| 6,371,921 | B1 | 4/2002 | Caro et al. |
| 6,377,829 | B1 | 4/2002 | Al-Ali |
| 6,388,240 | B2 | 5/2002 | Schulz et al. |
| 6,397,091 | B2 | 5/2002 | Diab et al. |
| 6,430,525 | B1 | 8/2002 | Weber et al. |
| 6,463,311 | B1 | 10/2002 | Diab |
| 6,470,199 | B1 | 10/2002 | Kopotic et al. |
| 6,501,975 | B2 | 12/2002 | Diab et al. |
| 6,515,273 | B2 | 2/2003 | Al-Ali |
| 6,525,386 | B1 | 2/2003 | Mills et al. |
| 6,526,300 | B1 | 2/2003 | Kiani et al. |
| 6,541,756 | B2 | 4/2003 | Schulz et al. |
| 6,542,764 | B1 | 4/2003 | Al-Ali et al. |
| 6,580,086 | B1 | 6/2003 | Schulz et al. |
| 6,584,336 | B1 | 6/2003 | Ali et al. |
| 6,597,933 | B2 | 7/2003 | Kiani et al. |
| 6,606,511 | B1 | 8/2003 | Ali et al. |
| 6,632,181 | B2 | 10/2003 | Flaherty et al. |
| 6,640,116 | B2 | 10/2003 | Diab |
| 6,643,530 | B2 | 11/2003 | Diab et al. |
| 6,650,917 | B2 | 11/2003 | Diab et al. |
| 6,654,624 | B2 | 11/2003 | Diab et al. |
| 6,658,276 | B2 | 12/2003 | Kianl et al. |
| 6,671,531 | B2 | 12/2003 | Al-Ali et al. |
| 6,678,543 | B2 | 1/2004 | Diab et al. |
| 6,684,090 | B2 | 1/2004 | Ali et al. |
| 6,697,656 | B1 | 2/2004 | Al-Ali |
| 6,697,658 | B2 | 2/2004 | Al-Ali |
| RE38,476 | E | 3/2004 | Diab et al. |
| 6,699,194 | B1 | 3/2004 | Diab et al. |
| 6,714,804 | B2 | 3/2004 | Al-Ali et al. |
| RE38,492 | E | 4/2004 | Diab et al. |
| 6,725,075 | B2 | 4/2004 | Al-Ali |
| 6,745,060 | B2 | 6/2004 | Diab et al. |
| 6,760,607 | B2 | 7/2004 | Al-Ali |
| 6,770,028 | B1 | 8/2004 | Ali et al. |
| 6,771,994 | B2 | 8/2004 | Kiani et al. |
| 6,792,300 | B1 | 9/2004 | Diab et al. |
| 6,813,511 | B2 | 11/2004 | Diab et al. |
| 6,816,741 | B2 | 11/2004 | Diab |
| 6,822,564 | B2 | 11/2004 | Al-Ali |
| 6,826,419 | B2 | 11/2004 | Diab et al. |
| 6,830,711 | B2 | 12/2004 | Mills et al. |
| 6,850,787 | B2 | 2/2005 | Weber et al. |
| 6,850,788 | B2 | 2/2005 | Al-Ali |
| 6,852,083 | B2 | 2/2005 | Caro et al. |
| 6,861,639 | B2 | 3/2005 | Al-Ali |
| 6,898,452 | B2 | 5/2005 | Al-Ali et al. |
| 6,920,345 | B2 | 7/2005 | Al-Ali et al. |
| 6,931,268 | B1 | 8/2005 | Kiani-Azarbayjany et al. |
| 6,934,570 | B2 | 8/2005 | Kiani et al. |
| 6,939,305 | B2 | 9/2005 | Flaherty et al. |
| 2004/0087846 | A1 * | 5/2004 | Wasserman .................. 600/323 |

OTHER PUBLICATIONS

Denis H. Jablonka, et al. "*Ear Plethysmographic Changes during Hemodialysis*," American Society of Anesthesiologist Annual Meeting (Oct. 23-27, 2004) Abstract a-588; Sep. 5, 2004.

Tamara Seidl, et al., "*Does Red Blood Cell Transfusion Change the Near Infra Red Photoplethysmography Signal in Infants?*" Intensive Care Medicine, vol. 30, No. 9, pp. 1602-1606, Aug. 2004.

Micha Shamir, et al., "*Plethysmographic Waveform Variation as an Indicator to Hypovolemia*," Anesthesia-Analgesia 2003; 97:602-603.

M. Shamir, et al., "*Pulse Oximetry Plethysmographic Waveform During Changes in Blood Volume*," British Journal of Anaesthesia, vol. 82, Issue 2, 178-181 (1999).

Kenneth Swank, "*Trauma Fluid Resuscitation*," 2003 Handout—Colorado Review of Anesthesia & Ski Holiday (CRASH), Dept. of Anesthesiology, University of Colorado School of Medicine.

Michiaki Yamakage, et al., "*Can Variation of "Pulse Amplitude Value" Measured by a Pulse Oximeter Predict Intravascular Volume?*" American Society of Anesthesiologists Annual Meeting (Oct. 23-27, 2004) Abstract A-582; Sep. 5, 2004.

\* cited by examiner

NONINVASIVE HYPOVOLEMIA MONITOR

CROSS-REFERENCE TO RELATED APPLICATIONS

This application relates to and claims the benefit of U.S. Provisional Application No. 60/607,562 entitled Noninvasive Hypovolemia Monitor, filed Sep. 7, 2004 and incorporated by reference herein.

BACKGROUND OF THE INVENTION

Pulse oximetry, a widely accepted noninvasive procedure for measuring the oxygen saturation level of arterial, blood, is responsive to pulsatile blood flowing within a fleshy tissue site. FIG. 1 illustrates the standard plethysmograph waveform 100, which can be derived from a pulse oximeter and corresponding pulse oximetry sensor. The sensor attaches to and illuminates a peripheral tissue site, such as a finger tip. The plethysmograph waveform 100 illustrates light absorption at the tissue site, shown along the y-axis 101, versus time, shown along the x-axis 102. The total absorption includes static absorption 110 and variable absorption 120 components. Static absorption 110 is due to tissue, venous blood and a base volume of arterial blood. Variable absorption 120 is due to the pulse-added volume of arterial blood. That is, the plethysmograph waveform 100 is a visualization of the tissue site arterial blood volume change over time, and is a function of heart stroke volume, pressure gradient, arterial elasticity and peripheral resistance. The ideal waveform pulse 130 displays a broad peripheral flow curve, with a short, steep inflow phase 132 followed by a 3 to 4 times longer outflow phase 134. The inflow phase 130 is the result of tissue distention by the rapid blood volume inflow during ventricular systole. During the outflow phase 130, blood flow continues into the vascular bed during diastole. The plethysmograph baseline 140 indicates the minimum basal tissue perfusion.

As shown in FIG. 1, a pulse oximetry sensor does not directly detect absorption, and hence does not directly measure the standard plethysmograph waveform 100. Rather, a pulse oximeter sensor generates a detected light intensity signal. However, the standard plethysmograph 100 can be derived from the detected intensity signal because detected intensity is merely an out of phase version of light absorption. That is, the peak detected intensity occurs at minimum absorption 136, and minimum detected intensity occurs at maximum absorption 138. Further, a rapid rise in absorption 132 during the inflow phase of the plethysmograph is reflected in a rapid decline in intensity, and the gradual decline 134 in absorption during the outflow phase of the plethysmograph is reflected in a gradual increase in detected intensity. A pulse oximetry sensor is described in U.S. Pat. No. 6,088,607 entitled Low Noise Optical Probe. A pulse oximetry monitor is described in U.S. Pat. No. 6,650,917 entitled Signal Processing Apparatus. Both of these patents are assigned to Masimo Corporation, Irvine, Calif. and incorporated by reference herein.

SUMMARY OF THE INVENTION

FIG. 2 illustrates a hypovolemic plethysmograph waveform 200. Hypovolemia is an abnormal decrease in blood volume, often caused from blood loss during surgery or due to an injury. Under hypovolemic conditions, a respiration-induced cyclical variation occurs in a plethysmograph baseline 240. This cyclical variation 240 is particularly evident in patients undergoing positive ventilation. The amount of cyclical variation correlates to patient blood volume, i.e. the less blood volume the greater the cyclical variation in the plethysmograph waveform. As such, gauging cyclical variation, as described in detail with respect to FIGS. 3-5, below, allows a hypovolemia monitor to advantageously generate a noninvasive hypovolemia indication or blood volume measure.

One aspect of a hypovolemia monitor comprises a plethysmograph input responsive to light intensity after absorption by fleshy tissue and a measurement of respiration-induced variation in the input. The measurement is normalized and converted into a hypovolemia parameter. The plethysmograph may be generated by a pulse oximeter, and an audible or visual indication of hypovolemia may be provided. In one embodiment, an envelope of the plethysmograph is detected and a magnitude of the envelope is determined in order to measure the respiration-induced variation. In an alternative embodiment, a curve-fit is made to a locus of points on the plethysmograph and the variation magnitude is determined from a characteristic of the resulting curve. In yet another embodiment, a frequency spectrum of the plethysmograph is determined and a frequency component of that spectrum proximate a respiration rate is identified. The variation magnitude is calculated from the magnitude of that frequency component.

In other embodiments of the hypovolemia monitor, the normalized measurement is calculated by dividing the variation magnitude by an average value of the plethysmograph. Conversion is accomplished by constructing a calibration curve of hypovolemia parameter versus variation magnitude and using that calibration curve to determine the hypovolemia parameter from the normalized measurement. A percentage of normal total blood volume or a percentage of total blood volume loss may be displayed based upon the hypovolemia parameter. An audible alarm or a visual alarm indicating a hypovolemia condition may also be generated.

Another aspect of a hypovolemia monitor is a variation function having a sensor input and generating a variation parameter. The sensor input is responsive to light intensity after absorption by fleshy tissue and provides a measure of respiration-induced cyclical variation in the sensor input. A normalization function is applied to the variation parameter so as to generate a normalized variation parameter responsive to an average value of the sensor input. A conversion function is applied to the normalized variation parameter so as to generate a hypovolemia parameter responsive to blood volume of a living subject. In one embodiment, the variation function comprises an envelope detector adapted to determine an envelope of the sensor input and a magnitude processor configured to calculate a magnitude of the envelope. In another embodiment, the variation function comprises a curve-fit processor adapted to determine a locus of the sensor input representative of the cyclical variation. A magnitude processor is configured to calculate a magnitude of the cyclical variation from the locus. In yet another embodiment, the variation function comprises a frequency transform processor configured to generate a frequency spectrum of the sensor input. A frequency component processor is configured to determine the magnitude of a frequency component of the spectrum corresponding to a respiration rate of the living subject.

In other embodiments, the normalization function calculates the magnitude divided by the average value so as to generate a normalized magnitude. The conversion function comprises a look-up table containing a curve representing a hypovolemia parameter versus the normalized magnitude. In a particular embodiment, the hypovolemia parameter corresponds to a percentage blood volume loss of the living subject.

A further aspect of a hypovolemia monitor comprises a variation means, a normalization means and a conversion means. The variation means is for measuring a magnitude of respiration-induced cyclical variations in an input plethysmograph. The normalization means is for normalizing the magnitude relative to a DC value of the plethysmograph. The conversion means is for translating the normalized magnitude to a hypovolemia parameter responsive to blood volume loss in a living subject.

DETAILED DESCRIPTION OF THE PREFERRED EMBODIMENTS

Figure 1:
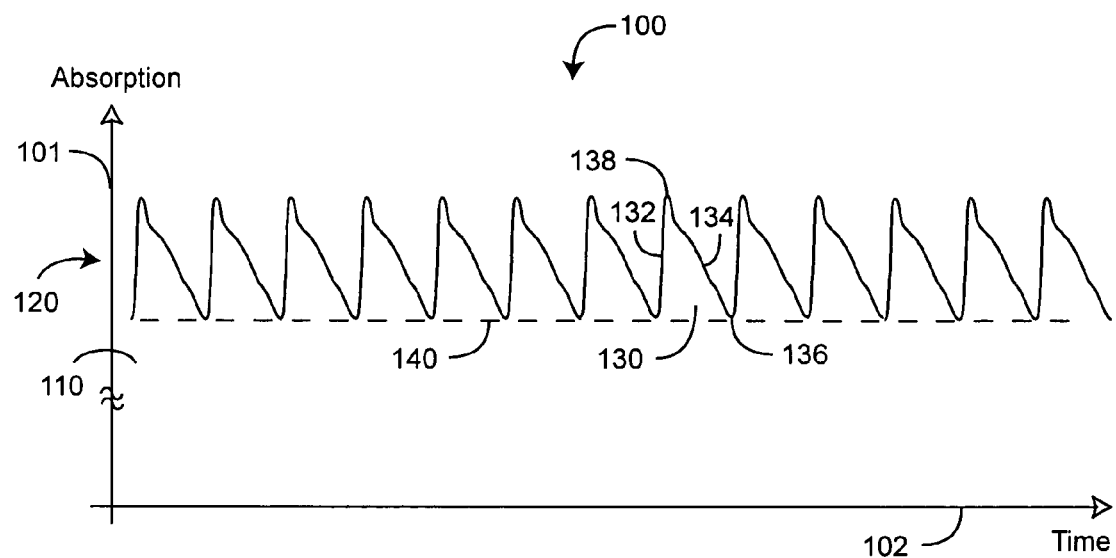
FIG. 1 is an absorption versus time graph of a standard pulse oximeter plethysmograph.
Figure 3:
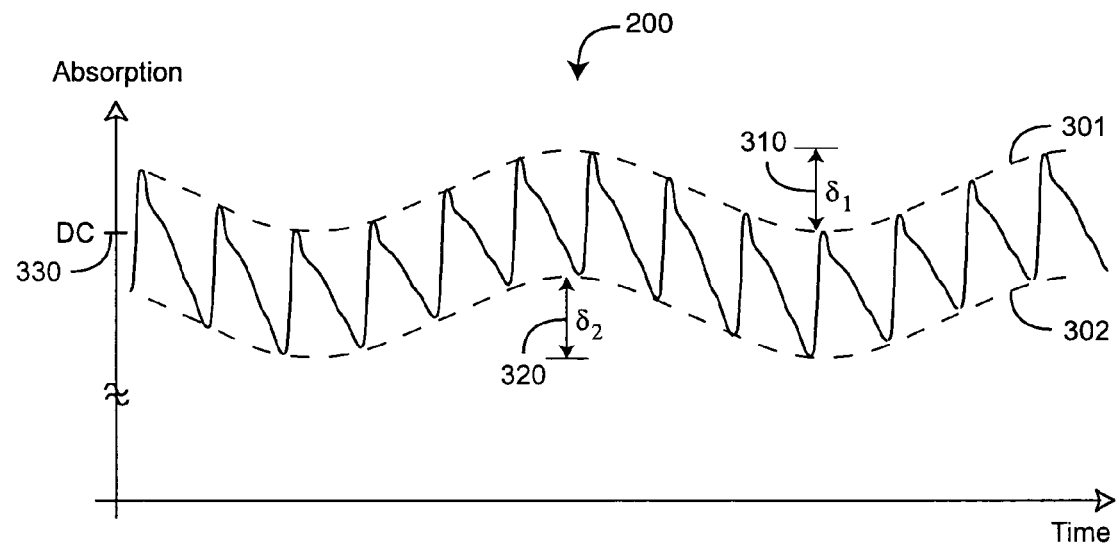
FIG. 3 is an absorption versus time graph of a plethysmograph envelope magnitude measure of cyclical variation.

FIG. 3 illustrates a plethysmograph envelope magnitude measure for the cyclical variation of a plethysmograph 200. In one embodiment, an upper envelope 301 of the plethysmograph 200 is determined. For example, the upper envelope 301 may be the locus of absorption maximums (peaks) 138 (FIG. 1) of each pulse 130 (FIG. 1). A variation parameter $\delta_1$ 310, the magnitude of the upper envelope 301, is determined, for example, from the delta between the highest peak and the lowest peak. The variation parameter 310 is normalized, e.g. by calculating the ratio of $\delta_1$ 310 over the DC 330 (direct current) value or average value of the plethysmograph 200. A hypovolemia parameter 502 (FIG. 5) responsive to the normalized variation parameter $\delta_1$/DC is then advantageously derived so as to noninvasively indicate a blood volume status, as described with respect to FIG. 5, below.

As shown in FIG. 3, in another embodiment, a lower envelope 302 of the plethysmograph 200 is determined. For example, the lower envelope 301 may be the locus of absorption minimums (valleys) 136 (FIG. 1) of each pulse 130 (FIG. 1). A variation parameter $\delta_2$ 320 of the lower envelope 302 is determined as, for example, the delta between the highest valley and the lowest valley. The variation parameter 320 is normalized as described above and a hypovolemia parameter 502 (FIG. 5) responsive to the normalized variation parameter $\delta_2$/DC is then derived, as described with respect to FIG. 5, below.

Figure 4:
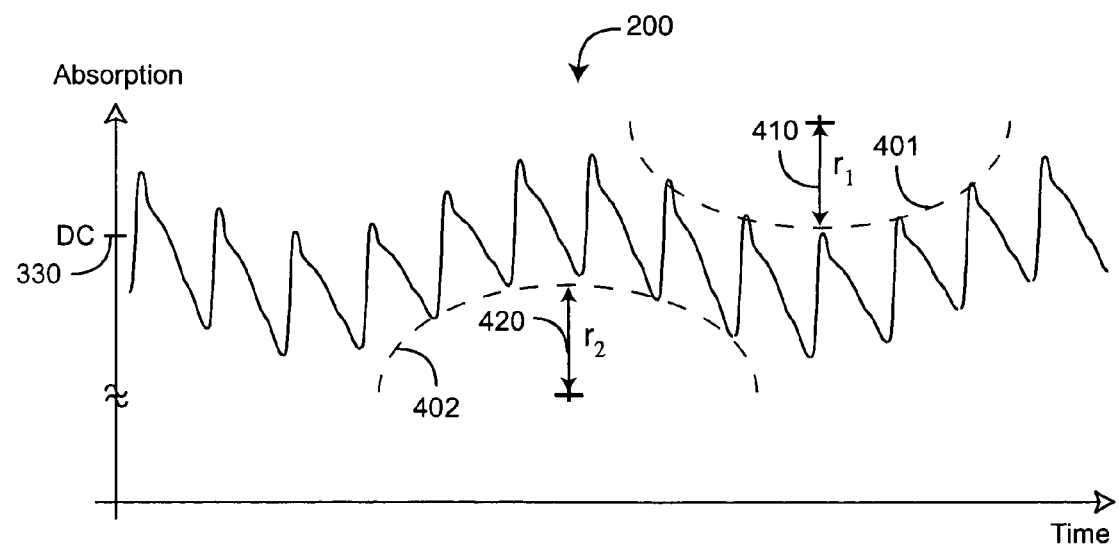
FIG. 4 is an absorption versus time graph of a plethysmograph envelope curve fit measure of cyclical variation.

FIG. 4 illustrates a plethysmograph curve-fit measure for the cyclical variation of a plethysmograph 200. In one embodiment, an upper curve-fit 401 of the plethysmograph 200 is determined. For example, the upper curve fit 401 may be a best fit of the absorption maximums (peaks) 138 (FIG. 1) of each pulse 130 (FIG. 1). In a particular embodiment, the curve 401 is an ellipse having a first axis length that is dependent on the respiration rate RR 250 (FIG. 2) and a variation parameter $r_1$ 410 related to a second axis length is determined by a best fit to the plethysmograph pulse peaks 138 (FIG. 1). The variation parameter $r_1$ 410 is normalized, e.g. by calculating the ratio of $r_1$ 410 over the DC 330 value. A hypovolemia parameter 502 (FIG. 5) responsive to the normalized variation parameter $r_1$/DC is then advantageously derived so as to noninvasively indicate a blood volume status, as described with respect to FIG. 5, below.

As shown in FIG. 4, in another embodiment, a lower curve-fit 402 of the plethysmograph 200 is determined. For example, the lower curve-fit 402 may be a best fit of the locus of absorption minimums (valleys) 136 (FIG. 1) of each pulse 140 (FIG. 1). In a particular embodiment, the curve 402 is an ellipse portion having a first axis length that is dependent on the respiration rate RR 250 (FIG. 2) and a variation parameter $r_2$ 420 related to a second axis length determined by a best fit to the plethysmograph pulse valleys 136 (FIG. 1). In another embodiment, the curve 402 is a portion of a circle having radius r, the variation parameter. The variation parameter $r_2$ 420 is normalized as described above. A hypovolemia parameter 502 (FIG. 5) responsive to the normalized variation parameter $r_2$/DC is then advantageously derived so as to noninvasively indicate a blood volume status, as described with respect to FIG. 5, below.

Figure 5:
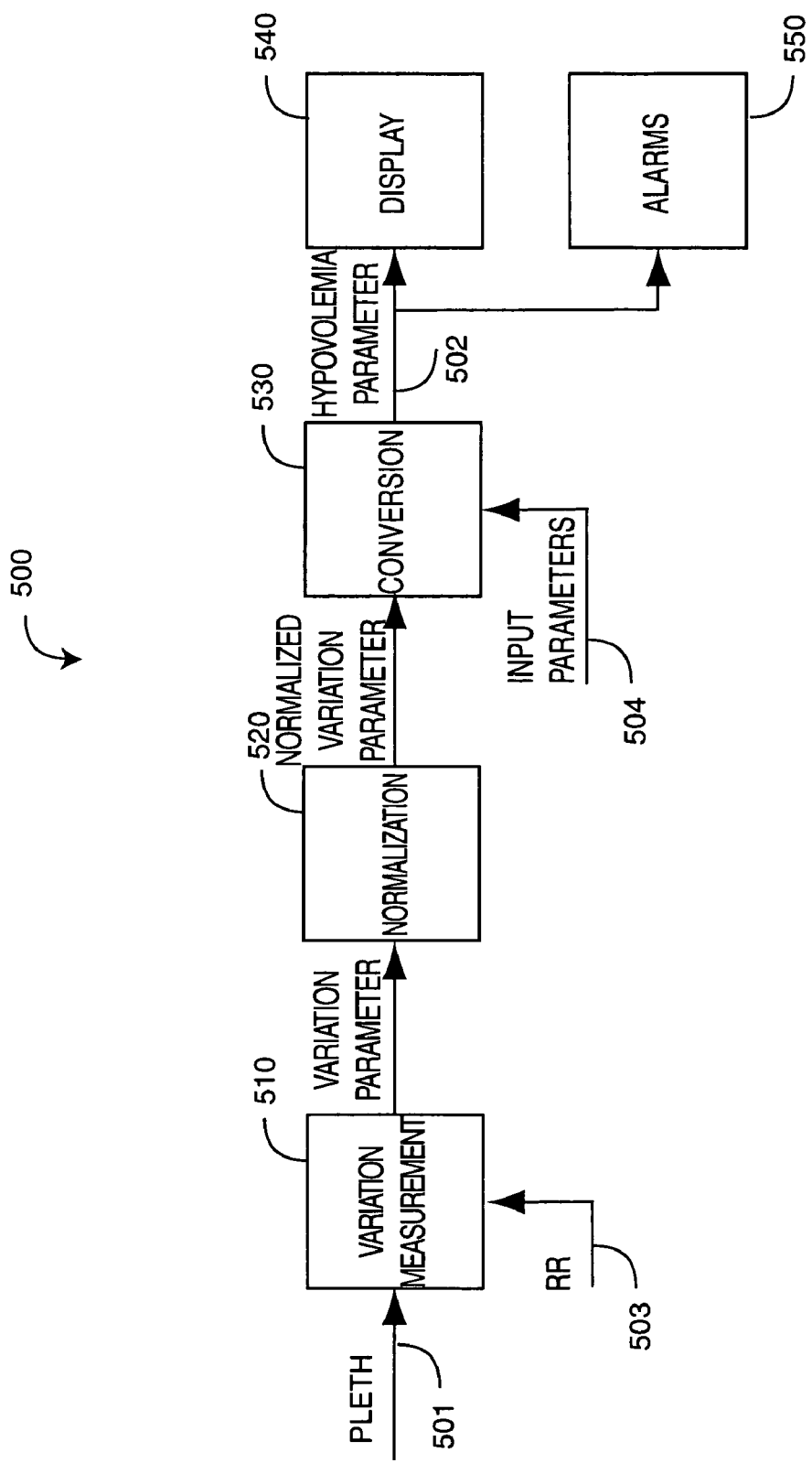
FIG. 5 is a block diagram of a noninvasive hypovolemia monitor.

FIG. 5 illustrates a noninvasive hypovolemia monitor 500, which is responsive to respiration-induced cyclical variations 240 (FIG. 2) in a plethysmograph. The hypovolemia monitor receives a plethysmograph waveform 501 input and provides a hypovolemia parameter 502 output indicative of a patient's blood volume status. In one embodiment, the plethysmograph 501 is an IR plethysmograph generated by a pulse oximeter. In other embodiments, the plethysmograph 501 is a photoplethysmograph or a pulse oximetry red plethysmograph. The hypovolemia monitor 500 has variation measurement 510, normalization 520 and conversion 530 functions. These functions can be performed with analog or digital circuitry or as processor-based algorithmic computations or a combination of the above.

Figure 2:
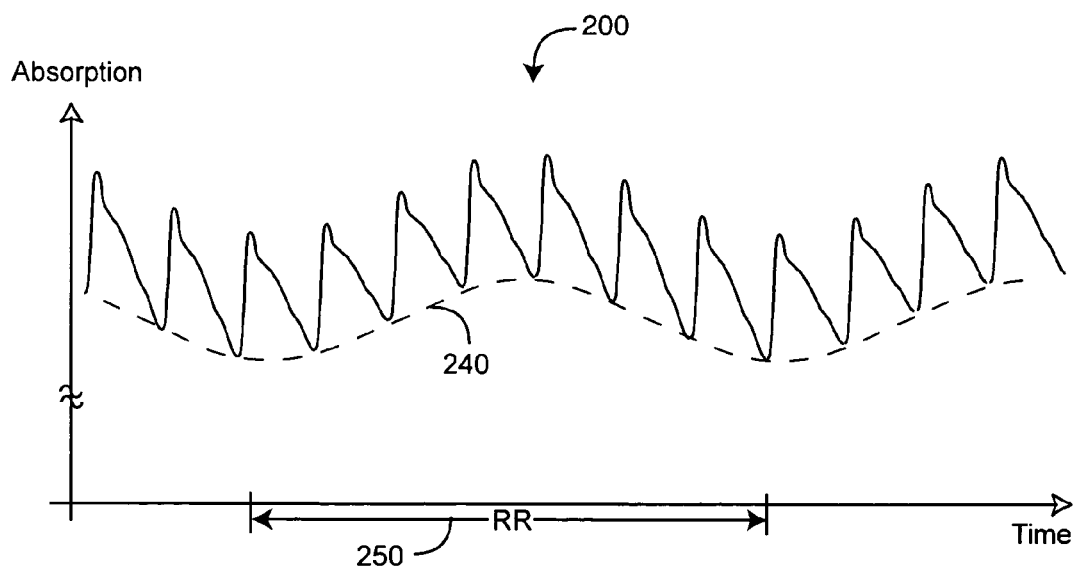
FIG. 2 is an absorption versus time graph of a plethysmograph exhibiting a respiration-induced, baseline cyclical variation.

As shown in FIG. 5, the variation measurement and normalization functions 510, 520 provide a relative measure of the degree of cyclical variation in the plethysmograph 200 (FIG. 2). In one embodiment, the variation measurement function 510 comprises a peak detector that determines the local maxima of each pulse of the plethysmograph waveform. The magnitude 310, 320 (FIG. 3), $\delta$, of the resulting waveform envelope is then calculated. The result is normalized 520 relative to an average or DC value 330 (FIG. 3) or similar value of the plethysmograph. The conversion function 530 converts the normalized variation measurement of the plethysmograph variation to a hypovolemia parameter 502. In one embodiment, the conversion function 530 comprises a calibration curve of a hypovolemia measure versus the normalized magnitude of respiration-induced cyclical variations. The calibration curve may be derived from a patient population using a standard blood volume test, such as indocyanine green (ICG) dye injection and dissipation. In a particular embodiment, the conversion function 530 is a lookup table containing one or more of such calibration curves. The hypovolemia parameter 502 advantageously provides a numerical value relating to patient blood volume status. As one example, the hypovolemia parameter 502 is a percentage measure of blood loss. As another example, the hypovolemia parameter 502 is measure of total blood volume in liters.

Also shown in FIG. 5, input parameters 504 can be utilized by the conversion function 530. In one embodiment, the input parameters 504 are patient type, such as adult, pediatric or neonate. In another embodiment, the input parameters include patient height and weight. In yet another embodiment, input parameters 504 are other physiological measurements, such as blood pressure.

Although the variation measurement and normalization functions are described above with respect to a time domain analysis, similar results can be achieved by a frequency domain analysis. For example, the variation measurement function 510 can be determined by performing a Fast Fourier Transform (FFT) or similar computation on the plethysmograph. In particular, the magnitude of the resulting spectral component at or near the respiration rate RR is determined. In one embodiment, respiration rate RR 503 is an input to the variation measurement function 510, as provided by a ventilator, a respiration belt transducer or similar device.

A noninvasive hypovolemia monitor has been disclosed in detail in connection with various embodiments. These embodiments are disclosed by way of examples only and are not to limit the scope of the claims that follow. One of ordinary skill in the art will appreciate many variations and modifications.

What is claimed is:

1. A method of monitoring a hypovolemia parameter of a patient with electronic oximetry monitoring circuitry configured to noninvasively and electronically monitor the patient, the method comprising the steps of:
   inputting a plethysmograph responsive to an output from a noninvasive oximetry sensor applied to said patient, said output responsive to light intensity after absorption by fleshy tissue;
   electronically measuring a respiration-induced variation in said input;
   electronically normalizing said measurement;
   electronically converting said normalized measurement into a numeric value indicating a blood volume level wherein said value indicates hypovolemia; and
   providing at least one of an audible indication and a visual indication of said value to a caregiver of said patient.

2. The hypovolemia monitoring method according to claim 1 wherein said inputting step comprises the substep of generating a pulse oximeter plethysmograph.

3. The hypovolemia monitoring method according to claim 2 wherein said measuring step comprises the substeps of:
   detecting an envelope of said plethysmograph; and
   determining a magnitude of said envelope.

4. The hypovolemia monitoring method according to claim 2 wherein said measuring step comprises the substeps of:
   fitting a curve to a locus of points on said plethysmograph;
   determining a magnitude of said variation from a characteristic of said curve.

5. The hypovolemia monitoring method according to claim 2 wherein said measuring step comprises the substeps of:
   determining a frequency spectrum of said plethysmograph;
   identifying a frequency component of said frequency spectrum proximate a respiration rate; and
   calculating a magnitude of said frequency component.

6. The hypovolemia monitoring method according to claim 3 wherein said normalizing step comprises the substeps of:
   calculating an average value of said plethysmograph; and
   dividing said magnitude by said average value.

7. The hypovolemia monitoring method according to claim 6 wherein said converting step comprises the substep of:
   constructing a calibration curve of said hypovolemia parameter versus variation magnitude;
   utilizing said calibration curve to determine said numeric value from said normalized measurement.

8. The hypovolemia monitoring method according to claim 7 wherein said providing step comprises the substep of displaying at least one of a percentage of normal total blood volume and a percentage of total blood volume loss based upon said numeric value.

9. The hypovolemia monitoring method according to claim 7 wherein said providing step comprises the substep of generating at least one of an audible alarm and a visual alarm indicating a hypovolemia condition.

10. A hypovolemia monitor comprising one or more processors programmed to include a variation function having a sensor input and generating a variation parameter, said sensor input responsive to light intensity after absorption by fleshy tissue, said variation parameter providing a measure of respiration-induced cyclical variation in said sensor input; the one or more processor also programmed to include a normalization function applied to said variation parameter so as to generate a normalized variation parameter responsive to an average value of said sensor input; and the one or more processor programmed to include a conversion function applied to said normalized variation parameter so as to generate a numeric value indicating a blood volume level wherein said value indicates hypovolemia; and
   an output providing at least one of an audible indication and a visual indication to one of a display and additional instrumentation.

11. The hypovolemia monitor according to claim 10 wherein said variation function comprises:
   an envelope detector adapted to determine an envelope of said sensor input; and
   a magnitude function configured to calculate a magnitude of said envelope.

12. The hypovolemia monitor according to claim 10 wherein said variation function comprises:
   a curve-fit function adapted to determine a locus of said sensor input representative of said cyclical variation; and
   a magnitude function configured to calculate a magnitude of said cyclical variation from said locus.

13. The hypovolemia monitor according to claim 10 wherein said variation function comprises:
   a frequency transform function configured to generate a frequency spectrum of said sensor input; and
   a frequency component function configured to determine the magnitude of a frequency component of said spectrum corresponding to a respiration rate of said living subject.

14. The hypovolemia monitor according to claim 11 wherein said normalization function calculates said magnitude divided by said average value so as to generate a normalized magnitude.

15. The hypovolemia monitor according to claim 14 wherein said conversion function comprises a look-up table containing a curve representing a numeric value versus said normalized magnitude.

16. The hypovolemia monitor according to claim 15 wherein said numeric value corresponds to a percentage blood volume loss of said living subject.

17. A hypovolemia monitor comprising:
   a variation means for measuring a magnitude of respiration-induced cyclical variations in an input plethysmograph;
   a normalization means for normalizing said magnitude relative to a DC value of said plethysmograph; and
   a conversion means for translating said normalized magnitude into a numeric value indicating a blood volume level wherein said value indicates hypovolemia.

* * * * *

UNITED STATES PATENT AND TRADEMARK OFFICE
CERTIFICATE OF CORRECTION

| | | |
|---|---|---|
| PATENT NO. | : 7,976,472 B2 | |
| APPLICATION NO. | : 11/221411 | |
| DATED | : July 12, 2011 | |
| INVENTOR(S) | : Kiani | |

It is certified that error appears in the above-identified patent and that said Letters Patent is hereby corrected as shown below:

At column 5, lines 62 to 63, Claim 7, please delete "said hypovolemia parameter" and insert therefore, --said numeric value--.

Signed and Sealed this
Seventeenth Day of January, 2012

David J. Kappos
*Director of the United States Patent and Trademark Office*